United States Patent
Ford et al.

(10) Patent No.: US 9,541,287 B2
(45) Date of Patent: Jan. 10, 2017

(54) COMBUSTION FURNACE AUTO CLEANER

(75) Inventors: Gordon C. Ford, St. Joseph, MI (US); Joshua N. Wetzel, Berrien Springs, MI (US); Kevin R. Brushwyler, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 747 days.

(21) Appl. No.: 13/198,746

(22) Filed: Aug. 5, 2011

(65) Prior Publication Data

US 2012/0036673 A1 Feb. 16, 2012

Related U.S. Application Data

(60) Provisional application No. 61/373,014, filed on Aug. 12, 2010.

(51) Int. Cl.
| | |
|---|---|
| *F23J 3/02* | (2006.01) |
| *F27B 17/02* | (2006.01) |
| *F27B 17/00* | (2006.01) |
| *G01N 31/12* | (2006.01) |
| *H05B 3/62* | (2006.01) |

(52) U.S. Cl.
CPC ............... *F23J 3/02* (2013.01); *F27B 17/02* (2013.01); *F27B 17/00* (2013.01); *G01N 31/12* (2013.01); *H05B 3/62* (2013.01)

(58) Field of Classification Search
CPC .......... F27B 17/02; F27B 17/00; G01N 31/12; H05B 3/62; F23J 3/02
USPC ................................ 422/78; 15/104.095, 304
See application file for complete search history.

(56) References Cited

U.S. PATENT DOCUMENTS

| | | | | |
|---|---|---|---|---|
| 4,234,541 A | * | 11/1980 | Bredeweg et al. | 422/78 |
| 4,388,722 A | * | 6/1983 | Tanimoto | 373/118 |
| 5,110,554 A | * | 5/1992 | Tanimoto | 422/78 |
| 2012/0213244 A1 | * | 8/2012 | Latino et al. | 373/118 |

FOREIGN PATENT DOCUMENTS

| | | |
|---|---|---|
| JP | 6-117978 | 4/1994 |
| JP | 7-38963 | 7/1995 |
| JP | 2000266740 | 9/2000 |

OTHER PUBLICATIONS

US Publication No. 2011/0075696 entitled Easily Removable Combustion Tube, published on Mar. 31, 2011.

* cited by examiner

*Primary Examiner* — Lyle Alexander
*Assistant Examiner* — Bryan Kilpatrick
(74) *Attorney, Agent, or Firm* — Price Heneveld LLP (57) ABSTRACT

An automatic cleaning assembly for an analytical furnace is detachable from the filter chamber above the combustion tube. The cleaning assembly includes a rotating brush which is lowered through the filter chamber and into the combustion tube while a vacuum is drawn through the lower seal of the combustion tube. This results in a higher vacuum pressure differential and improved flow rate for removing dust from the filter of the furnace and the combustion tube.

38 Claims, 10 Drawing Sheets

COMBUSTION FURNACE AUTO CLEANER

CROSS-REFERENCE TO RELATED APPLICATIONS

This application claims priority under 35 U.S.C. §119(e) and the benefit of U.S. Provisional Application No. 61/373,014 entitled COMBUSTION FURNACE AUTO CLEANER, filed on Aug. 12, 2010, by Gordon C. Ford, et al., the entire disclosure of which is incorporated herein by reference.

BACKGROUND OF THE INVENTION

The present invention relates to a combustion furnace for an analyzer and particularly to an automatic cleaning system.

The combustion of inorganic solid samples using an induction furnace requires a pressurized oxygen-rich environment. A quartz combustion tube is typically used to maintain this pressurized environment. Additionally, a filter is typically positioned adjacent the combustion tube and in the analyte gas stream to eliminate combustion debris which could degrade downstream analytical components. In one furnace system, a specimen is placed in a crucible which is positioned within the combustion tube and heated by an induction coil for the combustion of the specimen. The gases emitted therefrom are subsequently analyzed for determining one or more constituent elements of the specimen. The combustion tube so used is capable of many cycles of operation; however, after each combustion, oxides and other contaminants typically expelled during the combustion process tend to coat the interior of the tube. Thus, through the analytical process, the combustion tube and filter become coated with dust and residue debris of combustion. Removal of these combustion byproducts is essential in maintaining quality analytical results, as well as extending sample throughput.

The cleaning of the combustion tube and an associated filter requires moving wire brushes through the internal surfaces of the combustion tube and filter. U.S. Pat. No. 4,234,541 issued Nov. 18, 1980, discloses an early design in which a manually manipulated brush was employed to loosen debris from the filter and combustion tube, which debris is subsequently collected.

In current designs, dust and combustion residue is collected on a vacuum dust door enclosing the lower end of the combustion tube when the crucible pedestal and lower seal assembly are lowered. In this prior art design, a manifold communicates with the combustion tube and is coupled to a vacuum source as a non-rotating cleaning brush is linearly extended through the filter and combustion tube. The debris is then transferred to a collection box. With this design, when cleaning is complete, the vacuum dust door swings open to allow for another analysis cycle. However, too often, a combustion crucible falls into the vacuum dust door and the door becomes jammed. If this occurs, the operator must partially disassemble and repair the system prior to continuing with additional analyses. Also, with the prior art design, the vacuum dust door and/or the lower seal cup can plug due to accumulation of combustion byproducts, requiring manual cleaning.

Accordingly, there exists a need for an improved analytical combustion furnace in which cleaning of the filter and tube are better managed.

SUMMARY OF THE INVENTION

The system of the present invention accomplishes this goal by providing a cleaning assembly which is easily detachable from the filter chamber above the combustion tube. The automatic cleaning assembly includes a brush which rotates as it is lowered through the filter chamber and into the combustion tube while a vacuum is drawn through the lower end of the combustion tube. This results in a higher pressure differential and improved flow rate for removing dust from the filter of the furnace and the combustion tube. Additionally, the system eliminates the prior art vacuum dust door and employs the existing lower seal assembly already associated with the analytical system. This design will also dislodge crucibles sticking to the combustion tube by sequencing the brush and lower seal assembly, thereby eliminating operator intervention. This cleaning system improves analytical results and also extends analytical throughput by reducing down time due to jammed crucibles and manual cleaning.

These and other features, objects and advantages of the present invention will become apparent upon reading the following description thereof together with reference to the accompanying drawings.

DETAILED DESCRIPTION OF THE PREFERRED EMBODIMENT

Figure 1:
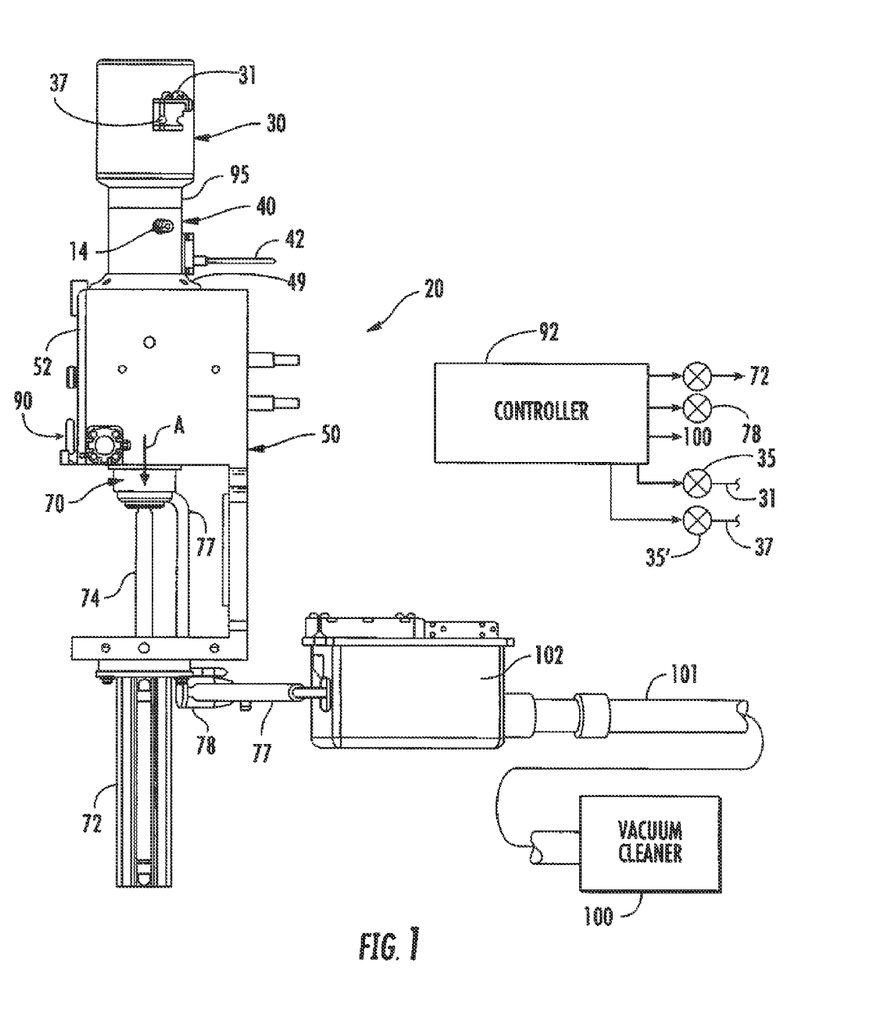
FIG. 1 is a right-side elevational view of an induction furnace embodying the auto cleaner of the present invention, partly shown in block form.
Figure 7:
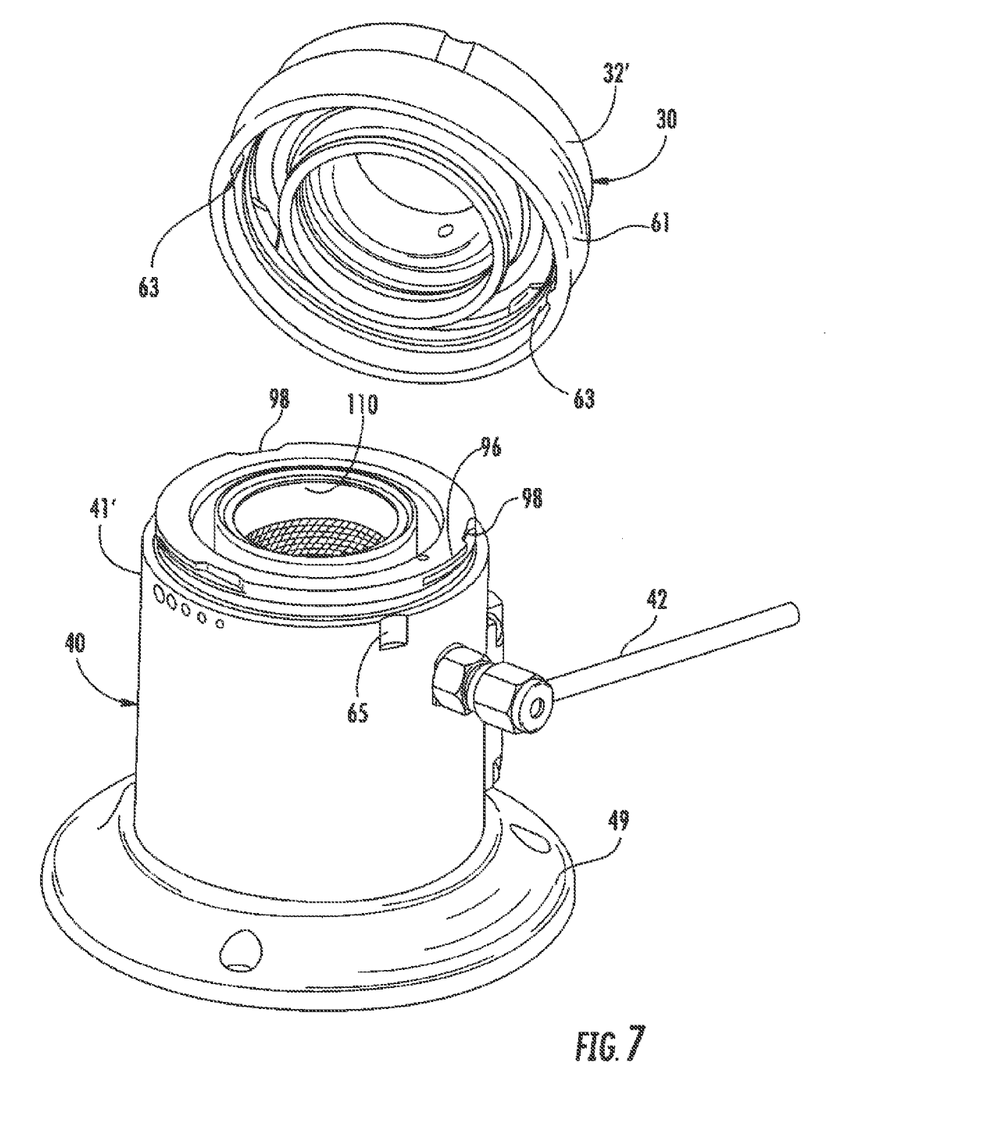
FIG. 7 is a perspective view of the bayonet mount between the auto cleaner housing and the filter assembly.
Figure 7A:
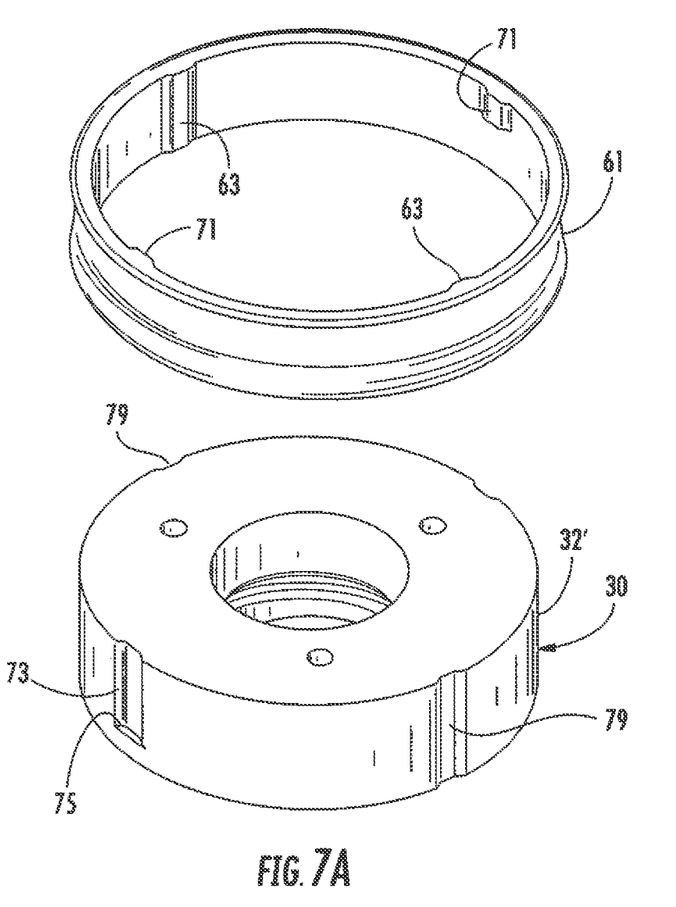
FIG. 7A is an exploded fragmentary perspective view of the locking ring and its relationship to cleaner assembly 30.

Referring initially to FIG. 1, there is shown an induction furnace assembly 20, including the auto cleaning mechanism of the present invention. The furnace 20 can be used with an analyzer similar to a carbon sulfur analyzer, Model No. CS600, available from Leco Corporation of St. Joseph, Mich. The induction furnace 20 includes a detachable auto cleaner assembly 30, which is removably mounted by a bayonet connection 95 (FIGS. 1 and 7) to a heated filter assembly 40, which is sealably secured to the combustion housing 50 by mounting flange 49. It is important that the bayonet mount 95 with mating flanges 96 and grooves 98 is proximate and above gas inlet 14 (FIG. 1) and outlet 42 and other connections related to the lower dust filter 40. Locating these connections on the lower side of the bayonet mount 95 significantly reduces the likelihood of leaks when the system is disassembled on a daily basis for maintenance. In order to lock the bayonet mount 95 in place during rotation of the cleaning brushes as described below, a keyed axially slideable torque locking ring 61 (FIGS. 2, 4, 5, 7, and 7A) is employed. As best illustrated in the fragmentary exploded view of FIG. 7A, ring 61 is captively and rotatably indexably held to the outer cylindrical wall 32' of the auto cleaner housing 30 by means of radially inwardly extending tabs 71 on ring 61, which slideably cooperate with grooves 73 in wall 32'. Grooves 73 terminate in a ledge 75 such that ring 61 can be raised above the intersection of housing 30 and filter assembly 40 at the bayonet mount but is captively held to housing 30, as seen in FIG. 7. When the cleaner assembly housing 30 is secured to the filter assembly housing 41 by the bayonet mount, ring 61 is lowered such that radially inwardly projecting tabs 63 in ring 61 slide through grooves 79 in wall 32' to engage grooves 65 in the outer cylindrical wall 41' of filter housing 41 (FIG. 7). This interlocks housings 30 and 40 to prevent the bayonet mount from inadvertently loosening during the cleaning process.

Figure 3:
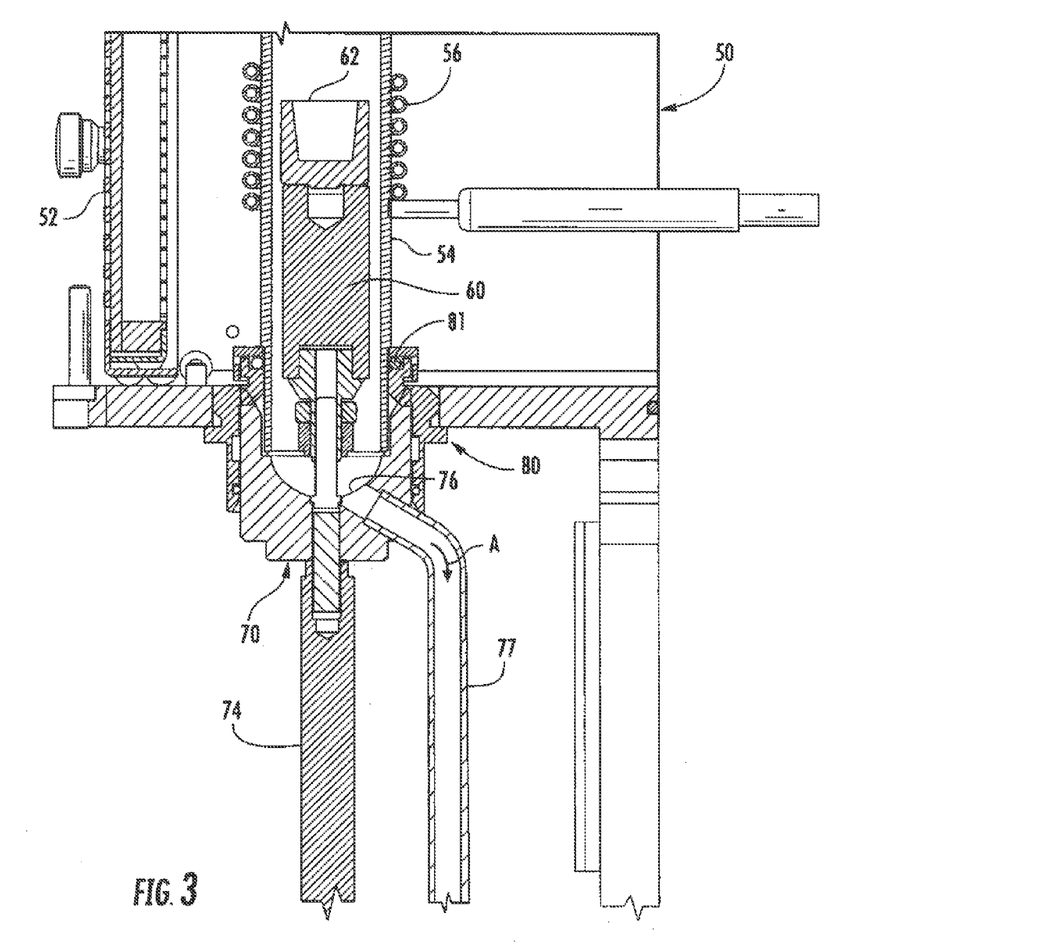
FIG. 3 is a vertical cross-sectional view of the induction furnace, combustion tube mounting system, and crucible pedestal located below the cleaning system shown in FIG. 2.
Figure 4:
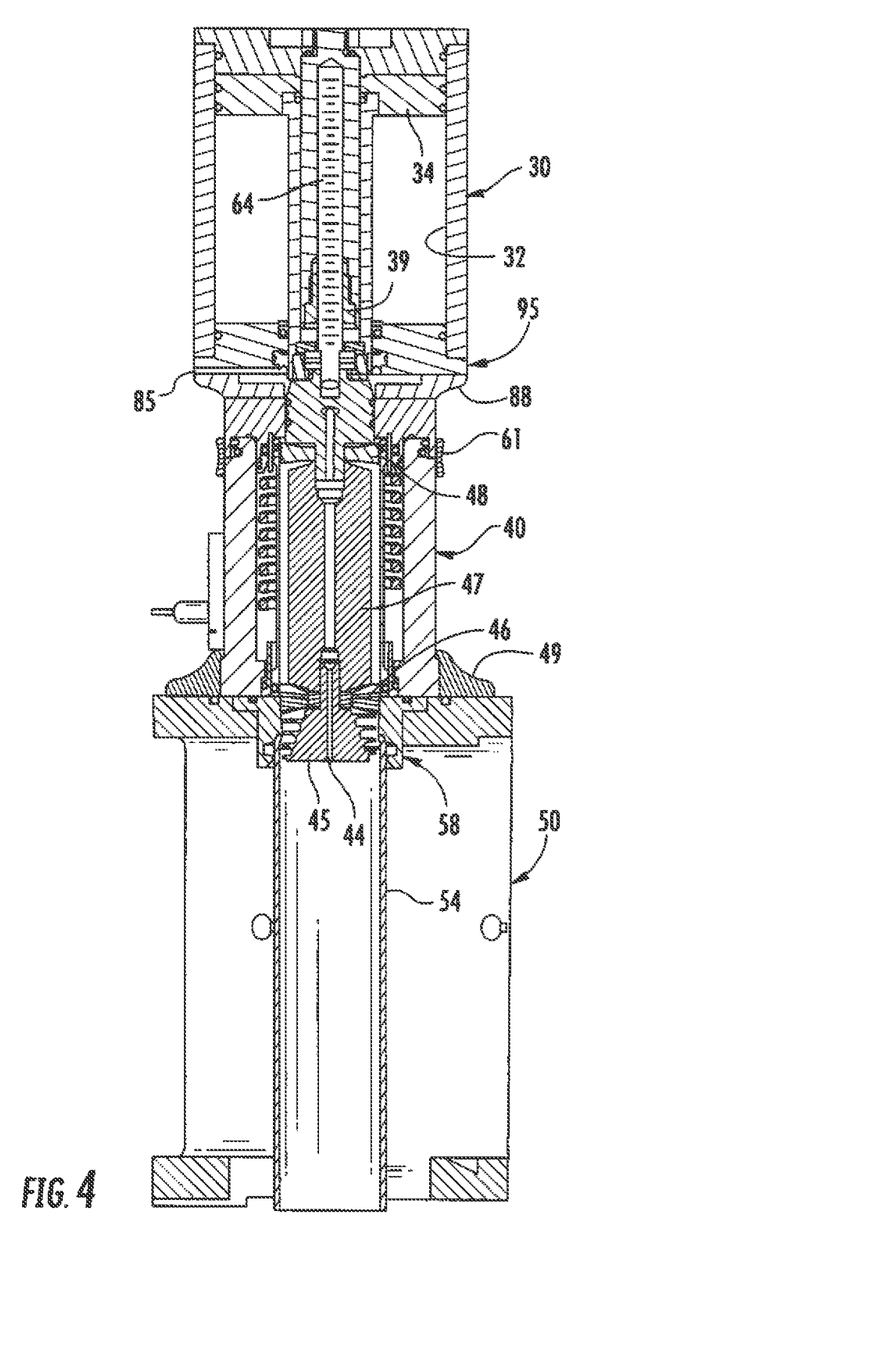
FIG. 4 is a vertical cross-sectional view of the auto cleaner mechanism and combustion furnace with the auto cleaner shown in a raised position.
Figure 5:
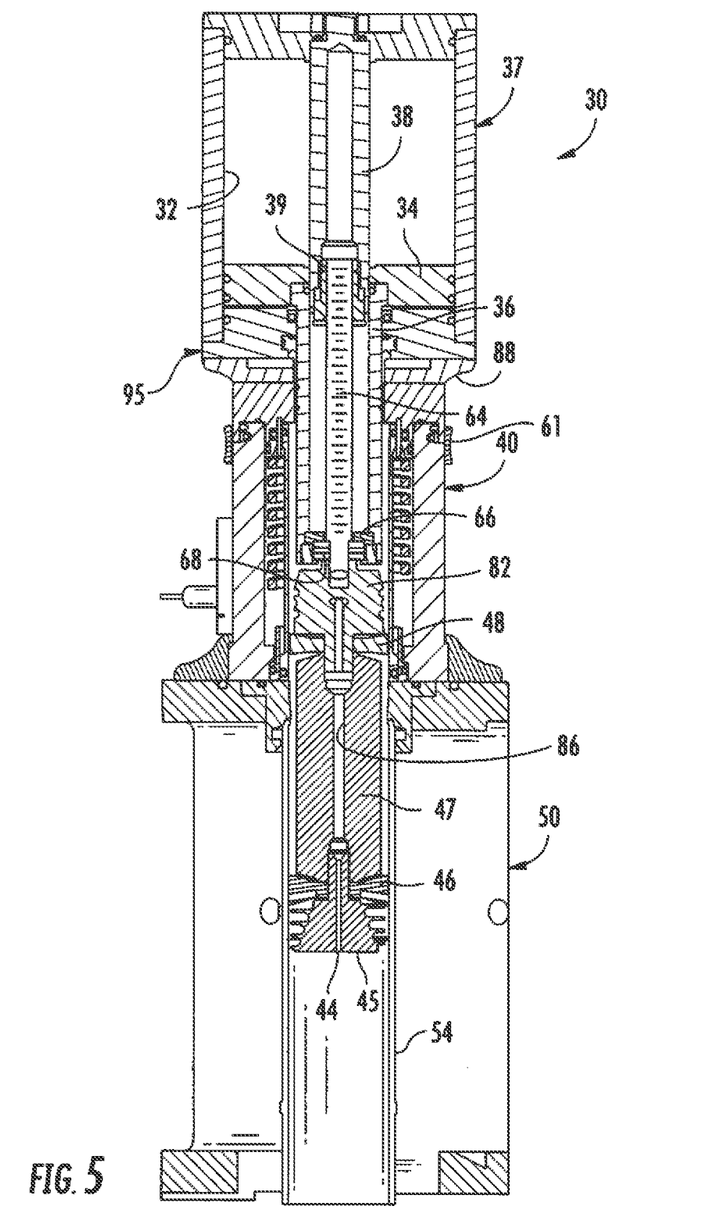
FIG. 5 is a vertical cross-sectional view of the structure of FIG. 4 with the auto cleaner shown in a lowered use position.
Figure 6:
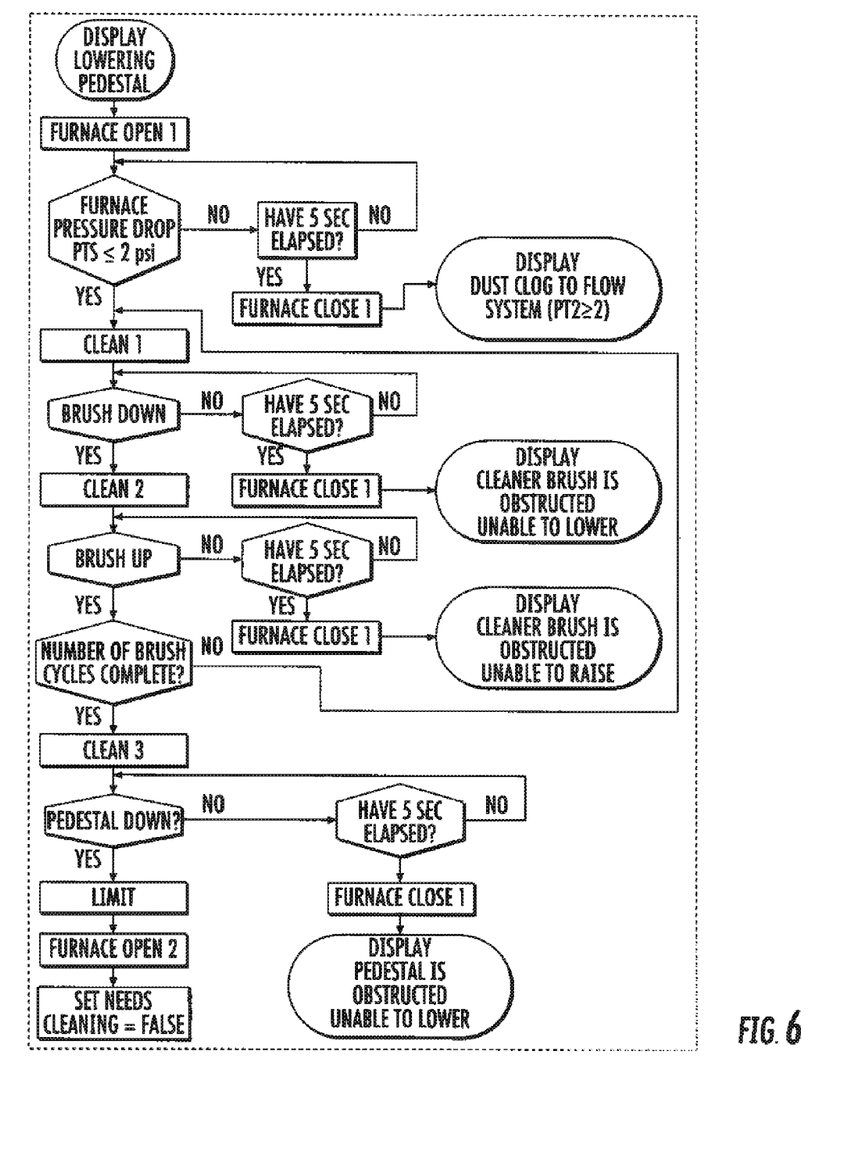
FIG. 6 is a flow diagram of the programming of the auto cleaner control for automatic operation.

Housing 50 includes a quickly removable door 52, which, when removed, exposes a combustion tube 54 surrounded by an induction coil 56 (FIG. 3). Tube 54 is sealably coupled to the lower end of filter assembly 40 by an upper seal assembly 58 (FIG. 4) in a conventional manner. A pedestal 60 (FIG. 3) holding a sample-holding crucible 62 is raised and lowered into combustion tube 54 through a cup-shaped assembly 70 by means of a pneumatic cylinder 72 having a rod 74 (FIGS. 1 and 3) coupled to assembly 70. In the position shown in FIG. 3, the cylinder rod 74 is in a raised position placing crucible 62 within the combustion tubes 54 for combustion of a sample therein by induction heating through RF coil 56.

Figure 8:
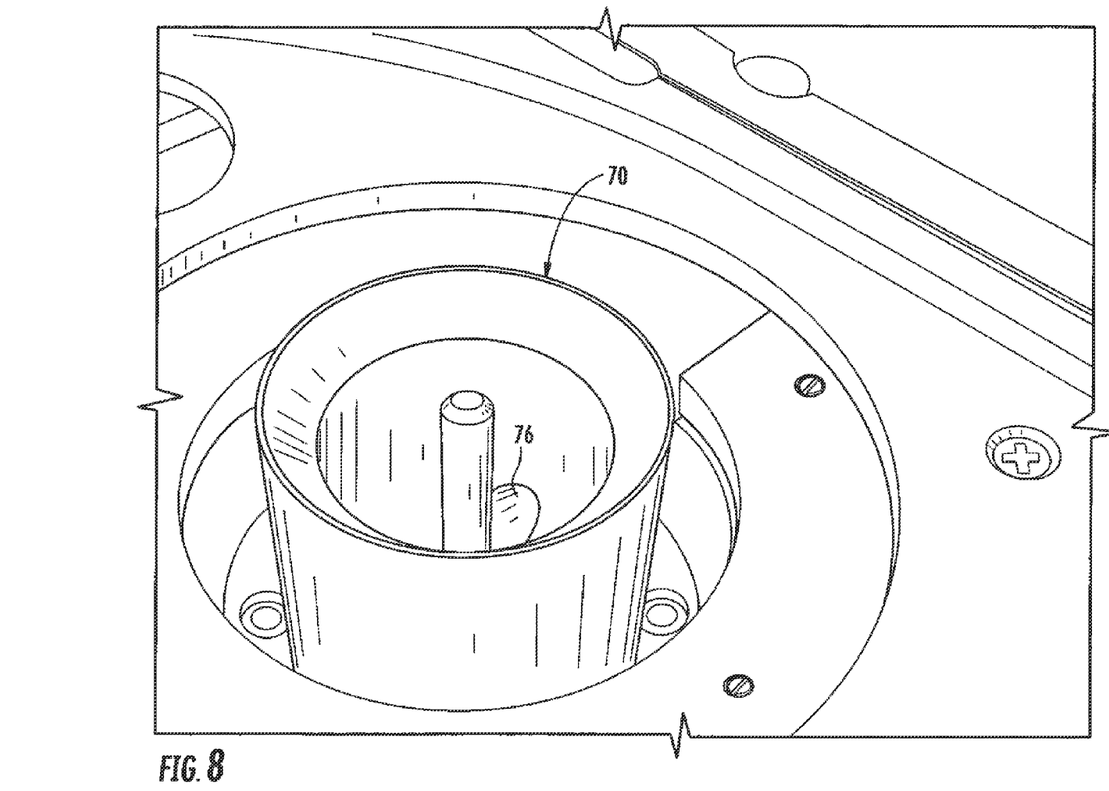
FIG. 8 is a perspective view of the cup-shaped lower seal body assembly, showing the vacuum aperture for removing debris.
Figure 9:
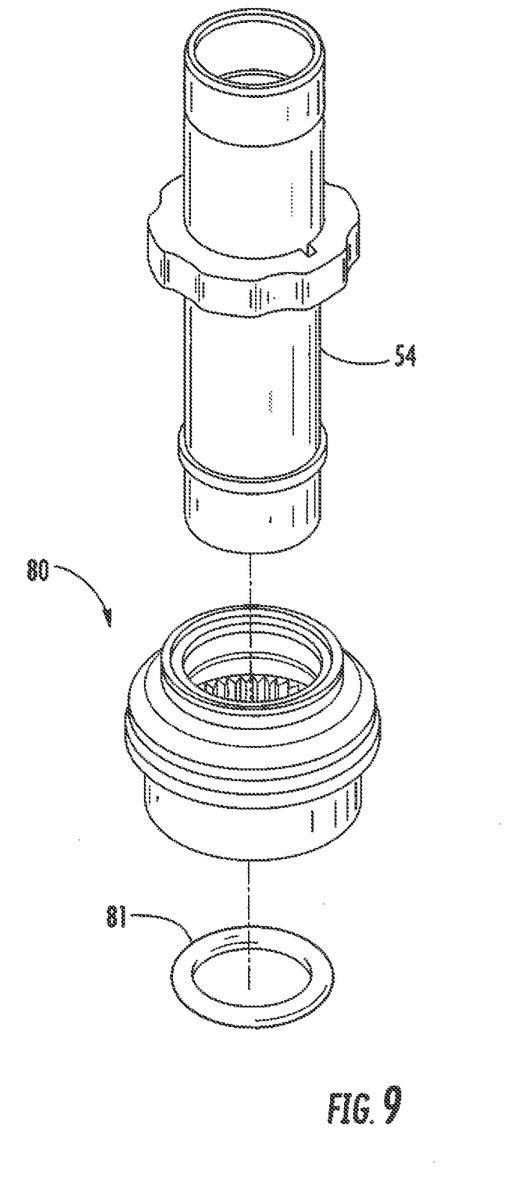
FIG. 9 is an exploded perspective view of the combustion tube base assembly and combustion tube.

A combustion tube base assembly 80 (FIGS. 3 and 9) includes an O-ring 81 which sealably couples the lower end of tube 54 to assembly 70 such that, during combustion of a sample, oxygen flows upwardly through a gas inlet 76 (FIG. 8) in assembly 70 to sweep byproducts of combustion into gas outlet 42 (FIG. 1) for analysis. Oxygen is also supplied to the central aperture 44 in spiral retainer 45 above combustion tube 54 (FIG. 2) by an oxygen inlet 14 (FIG. 1) and suitable sealed passageways 86 in inlet lance 82 and shaft extension 47 communicating with the aperture 44. During cleaning, dust and debris flow in a stream of air, as shown by arrow A in FIGS. 1 and 3, into assembly 70 and particularly through opening 76 (FIGS. 3 and 8), which leads to a vacuum hose 77 and a pneumatically actuated pinch valve 78 (FIG. 1) used in connection with a dust trap 102 coupled by hose 101 to a vacuum cleaner 100 for the vacuum removal of combustion debris in association with auto cleaner 30.

Housing 50 includes an easily removable combustion tube assembly 90 (FIG. 1) which cooperates with base assembly 80 and allows the combustion tube 54 to be easily withdrawn from the lower end of combustion housing 50, as described in detail in U.S. patent application Ser. No. 12/889,628, filed Sep. 24, 2010, and entitled EASILY REMOVABLE COMBUSTION TUBE, the disclosure of which is incorporated herein by reference.

The operation of cylinder 72 raises rod 74 which, in turn, raises a crucible 62 into the combustion tube 54 and seals the lower end of the tube by the sealed interface between assemblies 70 and 80 for the combustion of a sample and the subsequent analysis by the analyzer as well as during a cleaning sequence. The induction heater 56 heats a combustion sample to from about 1000° C. to about 1500° C. for the combustion of a sample under the influence of oxygen injected through the oxygen lance aperture 44 (FIGS. 2, 4, and 5) centered above the crucible during combustion.

The mechanism for extending the coaxially aligned spiral retainer 45, a first brush 46, a shaft extension 47, and a second brush 48 into the combustion tube 54 is now discussed in connection with FIGS. 2-6. The auto clean assembly 30 includes a cylinder 37 having a wall 32 housing a piston 34 coupled to a piston rod 36. The rod surrounds a stationary cylindrical guide sleeve 38 which captively holds a threaded drive nut 39 in fixed relationship to sleeve 38. Pneumatic pressure is applied to either the upper surface of piston 34 by supply conduit 31 (FIG. 1) which receives air pressure from a suitable source of air pressure to lower piston 34 or through conduit 37 to apply pressure to the lower surface of piston 34 for raising piston 34. Suitable pneumatic valves 35 and 35" are coupled to conduits 31 and 37 and are sequentially actuated by controller 92 programmed as shown, in part, by the flow diagram of FIG. 6 to operate the components of the system including cylinder 72, valve 78, cleaner 100, and valves supplying air or oxygen to passageways 86.

Figure 2:
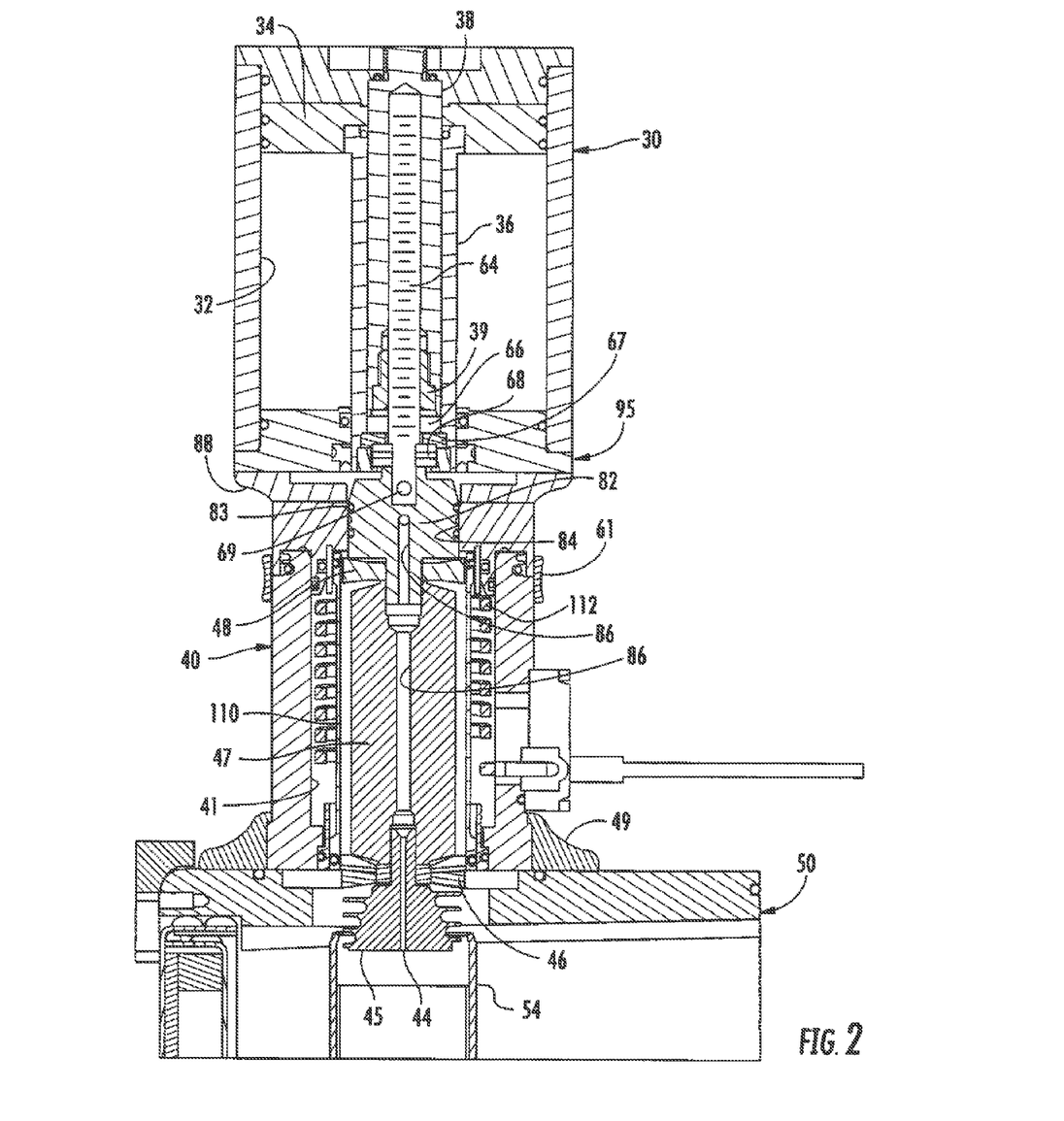
FIG. 2 is an enlarged detail drawing in vertical cross section of the auto cleaner positioned above the induction furnace.

The raising and lowering of piston 34 is translated to rotary movement of the brushes 46, 48 and spiral retainer 45 by a threaded lead screw 64 which is coupled to piston rod 36 by inlet lance 82 (FIG. 2). Thus, movement of piston 34 causes lead screw 64 to move up and down through the fixed drive nut 39 threadably coupled to lead screw 64 such that the lead screw also rotates and is supported by a thrust bearing 68 below retainer 66. A wiper seal 67 extends between the retainer 60 and thrust bearing 68. The lower end of lead screw 64 is coupled by a somewhat flexible pin coupling 69 (FIG. 2) to inlet lance 82 which includes O-ring seals 83 which sealably engage the cylindrical opening 84 at the upper end of filter assembly 40. When in a raised position, inlet lance 82 blocks the flow of air from passageways 85 (FIG. 4) in mounting and air inlet flange 88 coupling auto cleaning assembly 30 to filter assembly 40. When the cleaning brushes are lowered, the three 120° spaced passageways 85 in flange 88 are open to the atmosphere, allowing air to be drawn therein while a vacuum is applied to the chamber during cleaning through a vacuum source, such as a vacuum cleaner 100, coupled to a dust collection box 102 by conduit 101 (FIG. 1). The input through dust collection box 102 is coupled to vacuum hose 77 and pinch valve 78 coupled to the cup-shaped assembly 70 to draw a vacuum through aperture 76 (FIG. 8) which is sealably coupled by combustion tube base assembly 80 (FIG. 9) to the lower end of combustion tube 54. The pinch valve 78 on compressible conduit 77 allows a vacuum provided by cleaner 100 to provide a significant pressure differential between the atmosphere at the upper end of combustion tube 54 and filter assembly 40 and conduit 77. When pinch valve 78 is opened, a rush of cleaning air, aided by pulsed oxygen, through lance 82 dislodges debris, which is captured in vacuum cleaner 100. The flow path for the dust and debris collecting flow of air is shown by arrow A in FIGS. 1 and 3.

Thus, the actuation of piston 34 not only rotates and advances the cleaning brushes but also opens to the atmosphere through passageways 85 and the movement of inlet lance 82 a flow of air which transfers dust and debris from the induction furnace during the movement of the brushes downwardly and rotatably through the combustion tube 54. During the initiation of the cleaning cycle, the output tube 42 of the filter chamber, which typically carries byproducts of combustion to the analyzer, is momentarily reversed with a pulse of oxygen to assist in cleaning the dust filter 110 (FIG. 2) concentrically mounted within the cylindrical housing 41 of filter assembly 40. The dust filter is heated to approximately 120° C. by a surrounding coil heater 112 to remove moisture from material collected on the filter during the combustion process. The programming of the controller 92 (FIG. 1) to provide the sequence of operation of the various valves accomplishing the cleaning process as described above is shown in connection with the self-explanatory labeled flow diagram of FIG. 6.

It will become apparent to those skilled in the art that various modifications to the preferred embodiment of the invention as described herein can be made without departing from the spirit or scope of the invention as defined by the appended claims.

The invention claimed is:

1. A cleaning system for cleaning the combustion tube of an induction furnace of an analytical instrument, the cleaning system comprising:
an induction furnace having a first end and a second end;
a combustion tube, said combustion tube positioned between said first and second ends of said induction furnace, said combustion tube having an inner cylindrical wall and first and second ends;
a vacuum source selectively coupled to said first end of said induction furnace for drawing a vacuum on the induction furnace at said first end;
an induction coil surrounding said combustion tube for combusting an analytical sample positioned within said combustion tube;
a mechanical cleaning brush for abrading said inner cylindrical wall of said combustion tube;
a source of pressurized gas selectively coupled to said second end of said induction furnace and wherein said vacuum source is coupled to said first end of said induction furnace by a pinch valve, which is momentarily opened when said source of pressurized gas is coupled to provide a pressure differential between said second and first ends of said combustion tube; and
a drive coupled to said mechanical cleaning brush for selectively moving said cleaning brush into the combustion tube from said second end while said vacuum source removes debris from the induction furnace through said first end.

2. The cleaning system as defined in claim 1 and further including a filter housing positioned adjacent said induction furnace at said second end and wherein said filter housing includes a gas fitting, and pressurized gas is introduced into said filter housing through said fitting, wherein said brush is rotatably mounted in a housing coupled to said filter housing and wherein said housing includes a plurality of spaced-apart passageways for admitting air into said housing.

3. The cleaning system as defined in claim 2 wherein said brush is rotatably mounted in a housing coupled to said filter housing by a quick disconnect coupling.

4. The cleaning system as defined in claim 3 wherein said quick disconnect coupling is a bayonet mount.

5. The cleaning system as defined by claim 4 wherein said quick disconnect coupling includes a keyed sliding locking ring.

6. The cleaning system as defined in claim 1 wherein said induction furnace includes a cylindrical quartz combustion tube.

7. The cleaning system as defined in claim 6 wherein said drive comprises a piston coupled to a lead screw to which said brush is coupled and further including a fixed drive nut engaging said lead screw, such that, upon actuation of said piston, said brush rotates as it enters said combustion tube.

8. A cleaning system for the combustion tube of an induction furnace, the cleaning system comprising:
a combustion tube having an inner cylindrical wall;
upper and lower seal assemblies coupled to said combustion tube;
an induction coil surrounding said combustion tube;
a source of pressurized gas coupled to said combustion tube at said upper seal assembly;
a vacuum source selectively coupled to the lower seal assembly for drawing a vacuum on the combustion tube from a lower end thereof;
a rotatable brush positioned above said combustion tube in the area of said upper seal assembly, said brush having a diameter selected to engage said inner cylindrical wall of said combustion tube when said brush is moved into said combustion tube; and
a drive coupled to said brush for selectively lowering and rotating said brush into said combustion tube for abrading said inner cylindrical wall while said combustion tube is pressurized and a pinch valve coupled to said vacuum source is momentarily opened to provide a pressure differential between said second and first ends of said combustion tube to remove debris from a lower end of said combustion tube through said lower seal assembly.

9. The cleaning system as defined in claim 8 and further including a filter housing positioned above the combustion tube and wherein said filter housing includes a gas inlet, and pressurized gas is introduced into said filter housing on a side opposite said brush.

10. The cleaning system as defined in claim 9 wherein said filter housing includes a plurality of spaced-apart passageways for admitting air into said filter housing upon lowering said cleaning brush into said combustion tube.

11. The cleaning system as defined in claim 10 wherein said rotatable brush is mounted in a housing coupled to said filter housing by a bayonet mount.

12. The cleaning system as defined by claim 11 wherein said rotatable brush is mounted in a housing coupled to said filter housing by a quick disconnect coupling and said quick disconnect coupling includes a keyed sliding locking ring.

13. The cleaning system as defined in claim 8 wherein said vacuum source comprises a vacuum cleaner coupled to said lower seal assembly by a flexible conduit which is selectively closed and opened by said pinch valve.

14. The cleaning system as defined in claim 13 wherein said pinch valve is closely adjacent said lower seal assembly to minimize the purge volume of the furnace.

15. The cleaning system as defined in claim 14 wherein said induction furnace is enclosed in a cabinet with a removable door for access to said combustion tube.

16. An auto cleaner for use in an analytical induction furnace, the auto cleaner comprising:
an induction furnace including a combustion tube;
an induction coil surrounding said combustion tube;
a cleaner housing including a quick disconnect fitting for engaging an end of said induction furnace;
a piston mounted in said cleaner housing;
a source of pressurized fluid selectively coupled to said cleaner housing for moving said piston;
said piston coupled to a lead screw wherein said cleaner housing further includes a fixed drive nut threadably engaging said lead screw such that upon movement of said piston said lead screw rotates;

at least a first cleaning brush coupled to said lead screw remote from said piston such that upon movement of said piston, said cleaning brush rotates and extends linearly for cleaning said combustion tube in the induction furnace;
a source of pressurized oxygen coupled to an upper end of said combustion tube; and
a vacuum source selectively coupled to a lower end of said combustion tube for drawing a vacuum on the combustion tube, wherein said combustion tube is pressurized by said source of pressurized oxygen and a pinch valve coupled to said vacuum source is momentarily opened to provide a pressure differential between said upper and lower ends of said combustion tube to remove debris from said combustion tube.

17. The cleaner as defined in claim 16 and further including a fixed sleeve surrounding said lead screw and wherein said drive nut is mounted to said sleeve, and further including a cylindrical piston rod surrounding said sleeve such that, as said piston moves, said piston rod and brush extend away from said cleaner housing.

18. The cleaner as defined in claim 17 wherein said cleaner housing includes a wiper seal, such that, as said piston is actuated, said piston rod is guidably supported as it extends from said cleaner housing.

19. The cleaner as defined in claim 18 wherein said cleaner housing includes a thrust bearing coupled to said lead screw.

20. The cleaner as defined in claim 19 and further including an inlet lance extending between said at least a first brush and said threaded rod.

21. The cleaner as defined in claim 20 wherein said inlet lance is coupled to an end of said threaded rod by a flexible coupling.

22. The cleaner as defined in claim 21 and further including a shaft extension coupled to said inlet lance and a second brush is coupled to said shaft extension in spaced relationship to said at least a first brush.

23. The cleaner as defined in claim 22 wherein said shaft extension includes a central aperture coupled to said inlet lance for supplying a combustion gas to the combustion tube.

24. The cleaner as defined in claim 23 wherein a spiral retainer is coupled to said second brush on a side opposite said shaft extension.

25. The cleaner as defined in claim 24 and further including a filter housing having a gas inlet and a gas outlet and wherein said filter housing is coupled to said cleaner housing.

26. The cleaner as defined in claim 25 and further including an air inlet flange extending between said cleaner housing and said filter housing and including air inlet ports to allow the admission of air when said piston is actuated to extend said inlet lance to a position in said filter chamber.

27. The cleaner as defined in claim 26 and further including a vacuum source selectively coupled to said filter chamber when said piston is actuated to move one of said at least one brush or second brush into the combustion tube.

28. A cleaning system for the cylindrical wall of an induction furnace of an analytical instrument, the cleaning system comprising:
an induction furnace having a combustion tube with an internal cylindrical wall and a first end and a second end;
an induction coil surrounding said combustion tube;
a source of pressurized gas coupled to second end of said combustion tube;
a pedestal movable into said combustion tube through said first end for placing a sample holding crucible into said combustion tube for combustion of a sample for analysis;
a vacuum source selectively coupled to said first end for drawing a vacuum on said combustion tube at said first end;
a mechanical cleaning device for extending into said combustion tube from said second end; and
a drive coupled to said mechanical cleaning device for selectively moving said cleaning device into the combustion tube from said second end a distance sufficient for cleaning said internal cylindrical wall and dislodging any crucible which may be stuck in said combustion tube while said combustion tube is pressurized and a pinch valve coupled to said vacuum source is momentarily opened to provide a pressure differential between said second and first ends of said combustion tube to remove debris from the induction furnace through said first end.

29. The cleaning system as defined in claim 28 wherein said cleaning device includes a brush.

30. The cleaning system as defined in claim 29 and further including a filter housing positioned adjacent said induction furnace at said second end and wherein said filter housing includes a gas fitting, and pressurized gas is introduced into said filter housing through said fitting when said brush is moved into the combustion furnace.

31. The cleaning system as defined in claim 30 wherein said brush is rotatably mounted in a housing coupled to said filter housing by a quick disconnect coupling, wherein said housing includes a plurality of spaced-apart passageways for admitting air into said filter housing when said cleaning brush is lowered into said combustion tube.

32. The cleaning system as defined in claim 31 wherein said quick disconnect coupling is a bayonet mount.

33. The cleaning system as defined by claim 32 wherein said quick disconnect coupling includes a keyed sliding locking ring.

34. The cleaning system as defined in claim 33 wherein said vacuum source comprises a vacuum cleaner coupled to said first end by a flexible conduit which is selectively closed and opened by said pinch valve.

35. The cleaning system as defined in claim 28 wherein said induction furnace includes a cylindrical combustion tube having a cylindrical wall.

36. The cleaner as defined in claim 16 wherein said brush extends a distance sufficient to dislodge any crucible which may be stuck in said combustion tube.

37. A cleaning system for the combustion tube of an induction furnace having a combustion tube and upper and lower seal assemblies for the combustion tube, said cleaning system comprising:
a combustion tube having first and second ends;
a source of pressurized gas coupled to said second end of said combustion tube;
a vacuum source selectively coupled to the lower seal assembly for drawing a vacuum on the first end of said combustion tube from a lower end thereof;
a rotatable brush positioned above the second end of said combustion tube in the area of the upper seal assembly;
a drive coupled to said brush for selectively lowering and rotating said brush into said combustion tube for abrading debris from said combustion tube while said combustion tube is pressurized and a pinch valve coupled to said vacuum source is momentarily opened to remove debris from a lower end of said combustion tube through said lower seal assembly; and a filter housing positioned above the combustion tube and wherein said filter housing includes a gas inlet, and pressurized gas is introduced into said filter housing when said brush is moved toward the combustion tube, and wherein said rotatable brush is mounted in a housing coupled to said filter housing by a quick disconnect coupling.

38. The cleaning system as defined in claim 1 and further including a filter housing positioned adjacent said induction furnace at said second end and wherein said filter housing includes a filter and a gas fitting, and pressurized gas is introduced into said filter housing through said fitting on a side of said filter opposite said brush.

* * * * *